United States Patent [19]

Barthomeuf

[11] Patent Number: 4,593,149

[45] Date of Patent: Jun. 3, 1986

[54] PROCESS FOR SEPARATING ETHYLBENZENE FROM XYLENES BY SELECTIVE ADSORPTION ON A CESIUM SUBSTITUTED X ZEOLITE

[75] Inventor: Denise M. Barthomeuf, Lyons, France

[73] Assignee: Exxon Research and Engineering Co., Florham Park, N.J.

[21] Appl. No.: 666,193

[22] Filed: Oct. 29, 1984

[51] Int. Cl.$^4$ .................................................. C10C 7/13
[52] U.S. Cl. ................................ 585/828; 208/310 Z
[58] Field of Search ...................... 208/310 Z; 585/828

[56] References Cited

U.S. PATENT DOCUMENTS

| | | | |
|---|---|---|---|
| 2,882,244 | 4/1959 | Milton | 252/455 |
| 3,636,121 | 1/1972 | Stine et al. | 260/674 SA |
| 3,686,342 | 8/1972 | Neuzil | 260/674 SA |
| 3,686,343 | 8/1972 | Bearden, Jr. et al. | 260/674 SA |
| 3,813,452 | 5/1974 | Bieser | 585/828 X |
| 3,835,043 | 9/1974 | Geissler et al. | 210/31 C |
| 3,855,333 | 12/1974 | Neuzil | 260/674 SA |
| 3,867,470 | 2/1975 | Van Grinsven et al. | 260/674 SA |
| 3,878,127 | 4/1975 | Rosback | 252/455 Z |
| 3,894,108 | 7/1975 | Geissler | 260/674 SA |
| 3,903,187 | 9/1975 | Geissler | 260/674 SA |
| 3,943,182 | 3/1976 | Neuzil et al. | 585/828 |
| 3,969,276 | 7/1976 | Rosback | 585/828 X |
| 3,996,306 | 12/1976 | Korous et al. | 585/828 |
| 3,998,901 | 12/1976 | Neuzil et al. | 260/676 SA |
| 4,031,156 | 6/1977 | Geissler et al. | 208/310 Z X |
| 4,175,099 | 11/1979 | Geissler | 585/831 |
| 4,265,788 | 5/1981 | Ebitani | 252/455 Z |

FOREIGN PATENT DOCUMENTS 7602348  9/1976  Netherlands .................... 585/828

*Primary Examiner*—Andrew H. Metz
*Assistant Examiner*—Glenn A. Caldarola
*Attorney, Agent, or Firm*—E. Thomas Wheelock

[57] ABSTRACT

The invention relates to a process for selectively adsorbing ethylbenzene from a stream containing one or more isomeric xylenes. The ethylbenzene is adsorbed on Cs-substituted Type X zeolite. Certain alkyl substituted benzene desorbents give the zeolite good ethylbenzene selectivity over the xylenes.

17 Claims, No Drawings

4,593,149

PROCESS FOR SEPARATING ETHYLBENZENE FROM XYLENES BY SELECTIVE ADSORPTION ON A CESIUM SUBSTITUTED X ZEOLITE

FIELD OF THE INVENTION

This invention relates to a process for selectively separating ethylbenzene from a feedstream containing xylenes by using zeolite cesium substituted X and one or more of a group of organic desorbents. The preferred desorbents are alkyl-substituted benzenes.

BACKGROUND OF THE INVENTION

Some crystalline aluminosilicates, or zeolites, are useful as adsorbents in separating a particular hydrocarbon compound from hydrocarbon mixtures containing that compound. In particular, zeolites are widely used for selective separation of paraxylenes from mixtures containing other $C_8$ aromatic compounds such as meta-xylene, orthoxylene, or ethylbenzene. For example, U.S. Pat. Nos. 3,636,121; 3,686,342; 3,686,343; 3,835,043; 3,855,333; 3,878,127; 3,894,108; 3,903,187 and 4,265,788 are all directed towards methods of removing paraxylene from mixtures or of selectively separating paraxylene and ethylbenzene from mixtures containing other components, using various types of zeolites as adsorbents. Paraxylene is a commercially important aromatic hydrocarbon isomer since its use in the manufacture of terephthalic acid is a critical step in the subsequent production of various fibers such as Dacron.

This invention however relates to a process for separating ethylbenzene from a feed mixture containing ethylbenzene and at least one other xylene isomer and is therefore unrelated to paraxylene isomer separation processes. Additionally, in the process disclosed herein, ethylbenzene is selectively adsorbed in relation to the less selectively adsorbed xylene isomers.

While a separation of paraxylene from other xylene isomers is desirable in certain circumstances, it has become increasingly desirable to recover ethylbenzene from streams containing both ethylbenzene and xylene isomers. Ethylbenzene has great commercial importance since it is a building block in the production of styrene. Further, the cost of producing ethylbenzene by the reaction of benzene with ethylene has steadily increased. These costs have prompted research efforts in the recovery of ethylbenzene from various $C_8$ aromatic feedstreams which already contain ethylbenzene. Such feedstreams may be $C_8$ aromatic extracts resulting from various solvent extraction processes, or pyrolysis gasoline or reformed naphtha.

It is known that potassium substituted type Y zeolites selectively adsorb ethylbenzene from mixtures comprising ethylbenzene, metaxylene and orthoxylene using toluene as a desorbent. See for instance, U.S. Pat. No. 4,031,156. U.S. Pat. No. 3,998,901 suggests that ethylbenzene can be separated from xylene isomers using a type Y zeolite substituted with Sr and K wherein ethane or toluene is used as the desorbent. In U.S. Pat. No. 3,943,182 desorbents other than toluene are used as desorbents in selectively separating ethylbenzene from xylenes by use of a type X zeolite.

However, U.S. Pat. No. 3,686,342 suggests that type X and type Y zeolites are substantially equivalent in showing a preferred selectivity for paraxylene with respect to ethylbenzene, particularly when substituted with metals such as, inter alia, rubidium and cesium. Nonequilibrium absorption conditions are said to be the reason for the selective adsorptivity. In contrast, other U.S. patents suggest that RbX and CsX zeolites are known to adsorb selectively ethylbenzene over paraxylene. U.S. Pat. Nos. 3,943,182; 4,031,156; and 4,175,099 show RbX zeolites in such service and U.S. Pat. Nos. 3,867,470 and 3,943,182 show CsX zeolites. Consequently, the selectivity of such zeolites is not readily predictable and may in some instances depend upon the choice of desorbents for their selectivity. Moreover, the direction in which a zeolite's specific adsorptivity moves as a result of using a particular desorbent is even less predictable.

SUMMARY OF THE INVENTION

The invention disclosed herein is directed to a process for selectively adsorbing ethylbenzene from feedstreams containing both ethylbenzene and mixtures of xylenes. The process utilizes cesium substituted type X zeolites and certain desorbents. The desorbents may be generically described as monoalkylbenzenes having an alkyl group between $C_2$ and $C_{15}$ and dialkylbenzenes having alkyl substituents between $C_1$ and $C_{15}$. This combination of desorbent and zeolites produces simultaneously acceptable values for the selectivities of ethylbenzene over paraxylene or metaxylene or orthoxylene. These desorbents are important in that they increase each ethylbenzene selectivity factor with respect to the xylene isomers, particularly that of ethylbenzenes over orthoxylenes.

Ethylbenzene can be separated and recovered from a feedstream mixture containing at least one and preferably all isomeric xylenes by the process of (a) contacting the hydrocarbon mixture with a type X zeolite at least partially substituted with cesium cations, so that the contacting takes place under conditions to affect a selective adsorption of ethylbenzene by the zeolite, (b) passing through the zeolite, during or after the contacting step, a desorbent which produces a selectivity factor ($\gamma$EB/xylene) for each xylene which is greater than 1.5 to 2 under the same conditions, and which has a desorbent strength factor ($\gamma$eb/desorbent) in the range of 0.1 to 10, and (c) recovering from the zeolite a stream enhanced in the concentration of ethylbenzene relative to the isomeric xylenes.

The selectivity factor, which represents the selectivity of the adsorbent for ethylbenzene over a particular xylene, is defined by the expression:

$$\alpha \text{ eb/xylene isomer} = \frac{\text{amount of ethylbenzene in zeolite}}{\text{amount of ethylbenzene in non-adsorbed phase}} \times \frac{\text{amount of xylene isomer in non-adsorbed phase}}{\text{amount of xylene isomer in zeolite}}$$

The desorbent strength factor, which represents the selectivity of the adsorbent for ethylbenzene over the desorbent, is defined by the expression:

$$\alpha \text{ EB/desorbent} = \frac{\text{amount of ethylbenzene in zeolite}}{\text{amount of ethylbenzene in non-adsorbed phase}} \times \frac{\text{amount of desorbent in non-adsorbed phase}}{\text{amount of desorbent zeolite}}$$

DESCRIPTION OF THE PREFERRED EMBODIMENT

The feedstream mixtures which are applicable to the present invention comprise at least ethylbenzene and one xylene isomer. Preferably the feedstream contains ethylbenzene and all of the xylene isomers. In addition, the feedstream mixture may contain up to about 20%, but preferably less than about 10 volume percent, of non-aromatic components such as paraffins, cycloaliphatic of olefinic compounds. Such components will tend to be adsorbed by the zeolite in smaller amounts than the aromatic components. Irrespective of whatever else may be present in the mixture, the process embodies the technique of separating ethylbenzene from various xylenes.

The feedstream mixtures containing $C_8$ aromatics such as ethylbenzene, xylene isomers are generally obtained through such processes as reforming, pyrolysis and isomerization. The paraxylene isomer is often extracted from this mixture by the processes of crystallization, extraction, or selective adsorption, thus leaving a feedstream relatively rich in ethylbenzene, orthoxylene and metaxylene and substantially depleted in paraxylene. The process steps described herein as part of the invention may be used after a paraxylene separation process or preferably may be used before such a separation process. The latter method improves the efficiency of the overall process since the paraxylene recovered should then have no ethylbenzene impurity.

In the process described herein, the ethylbenzene is separated from the xylene isomers in the feedstream mixture by contacting the mixture with the zeolite adsorbent defined below such that the ethylbenzene is more selectively adsorbed than the xylene isomers. Concurrently with this contacting step, or subsequent thereto (if the operation is a batch operation), desorbents are passed through the zeolites to desorb the ethylbenzene-containing phase which has become absorbed on the zeolite.

The zeolite contacting step may be conducted in a batch or continuous mode of operation. For example, the adsorbent zeolite may be placed in a fixed bed which is intimately contacted with a feedstream mixture containing ethylbenzene and xylenes along with a desorbent or it may be placed in a fluidized bed which is contacted with a feedstream mixture and a desorbent in a continuous operation. The fluidized bed may be used with or without magnetic stabilization and with or without real or simulated co- or countercurrent flows. Where the adsorbent is employed in a static bed, the process may be semi-continuous, e.g., or operated as a pulsed chromatographic process. The adsorbent may be placed in a set of two or more static beds such that the feedstream mixture is contacted with one bed while the desorbent is passed through one of the others. In some instances, it may be desirable to remove a least-adsorbed component from the voids in a bed by flushing with a very weakly adsorbed material, e.g., a paraffin, before recovery of ethylbenzene by addition of a desorbent. Moving or simulated moving beds represent a preferred mode of operation because of the greater efficiency in the resulting separation.

Temperatures for contacting and desorption steps of the process herein may vary broadly depending, inter alia, on the desorbent used, but generally will range from about room temperature to about 300° C. Similarly operating pressures will vary considerably but generally will range from about atmospheric to about 30 atmospheres (3 megapascals) pressure.

The desorbent employed in the present invention may be defined as a compound which is characterized by its minimum ability to enhance the selectivity of CsX zeolites for separating ethylbenzene from xylene isomers, particularly from orthoxylene and paraxylene, and by maintaining those selectivities above about 2.0. The selectivity is expressed herein as a selectivity factor, designated $\gamma$EB/xylene isomer, which is defined above. The value of the selectivity factors should be as high as possible. Too low a factor will result in poor separation between two components.

Another parameter which characterizes the desorbent herein is the strength of the desorbent, which is expressed by a desorbent strength factor, designated $\gamma$EB/desorbent as defined above. This factor represents the ratio of the adsorption strength of the zeolite for the ethylbenzene to the adsorption strength of the zeolite for the desorbent. If the desorbent is too strong relative to ethylbenzene, e.g., so that the desorbent strength factor is less than 0.1, then both ethylbenzene and the xylenes will be eluted at a similar time. On the other hand, a desorbent having a desorbent strength factor of greater than about 10 will not compete favorably with the ethylbenzene, necessitating large volumes of desorbent to recover all the ethylbenzene. The ethylbenzene thus collected would be contained in a large amount of the desorbent so that an expensive and energy consuming distillation procedures would be required to recover the ethylbenzene. The desorbent strength factor ratio is preferably in the region of about 1 to about 2, but for the purposes herein should generally be in the range from about 0.1 to about 10.

The desorbents applicable to the process disclosed herein simultaneously increase the three selectivities $\gamma$eb/px, $\gamma$eb/mx and $\gamma$eb/ox as compared to the intrinsic zeolite selectivity and moreover give an acceptable $\gamma$eb/des value. They may be generically described as alkylbenzenes. The monoalkyl constituents may contain 2 to 15 carbon atoms. Specially preferred are alkylbenzenes especially those belonging to the group consisting of n-propylbenzene, and n-butylbenzene, n-pentylbenzene, n-heptylbenzene, isobutylbenzene, and n-nonylbenzene; most preferred is n-nonylbenzene. Dialkylbenzenes which offer superlative results include m-diethylbenzene, o-methyl-n-propylbenzene and p-methyl-n-propylbenzene. The alkyl substituents of the dialkylbenzenes may be between $C_1$ and $C_{15}$. In addition, mixtures of two or more desorbents which have the requisite characteristics may also be employed as desorbents desired. The desorbent may be diluted with a liquid inert material such as a paraffin or a cycloparaffin.

The zeolite type X can be represented in terms of mole oxides as represented by the following equation:

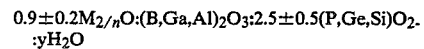

$$0.9 \pm 0.2 M_{2/n}O:(B,Ga,Al)_2O_3:2.5 \pm 0.5(P,Ge,Si)O_2.:yH_2O$$

where M represents Cs and optionally at least one other metal selected from the group consisting of Li, Na, Mg, K, n represent the average valence of M, and y is a value up to about 8 depending upon the identity of M and the degree of hydration of the crystalline zeolite. The Type X zeolite is generally described in U.S. Pat. No. 2,882,244.

After the feedstream mixture and desorbent have been contacted with a zeolite, the respective eluted product streams containing the various components are directed to separate recovery vessels. The stream recovered which is enhanced in the amount of ethylbenzene relative to xylene monomers in the mixture (due to the separation achieved by the adsorption and desorption operations) may be further processed to recover the ethylbenzene by, e.g., distillation, or other suitable recovery techniques.

The following examples further illustrate the efficacy of the present invention. In these examples all parts or percentages are given by weight and all temperatures are given in degrees Centigrade unless otherwise indicated.

EXAMPLE 1

Cesium substituted Type X zeolites were prepared from commercially available 13X and was ion exchanged with cesium by exchange with a cesium chloride solution, drying at 120° C., calcining at 550° C. under flowing nitrogen gas, cooling, reexchanging with a cesium solution, drying, calcining, reexchanging a third time and drying a third time. The zeolites were then calcined for at least 15 hours under flushing dry nitrogen at a temperature of at least 550° C. The resulting zeolites had 50 Cs cations and 36 Na cations per zeolite X unit cell.

About three hundred milligram samples of the dried zeolite were transferred each to a series of 2 ml vials sealed with a septum cap. To each bottle was added, by syringe, the respective feed in an amount representing the capacity of the zeolite. The vials were agitated at room temperature for 2 to 24 hours under ambient conditions and allowed to reach adsorption equilibrium. The vapor phase above the zeolite was analyzed by gas chromatography. Due to the selectivity of adsorption, the vapor pressures reflect the composition of the liquid phase in equilibrium with the zeolite. From the gas chromatograph peaks, the $\gamma$eb/xylene isomer peaks and $\gamma$eb/desorbent factors were calculated (see Tables 1 and 2).

TABLE 1

Selectivity ("") for $C_8$ Aromatics on $Cs_{50}Na_{36}X$
Feed: Equimolar $C_8$ Aromatics: Desorbent

| Desorbent | eb/px | eb/mx | eb/ox | eb/Des | $C_8$: Desorbent (by mole) |
|---|---|---|---|---|---|
| None | 3.3 | 4.1 | 1.8 | — | — |
| Benzene | 1.3 | 1.6 | 3.0 | 0.15 | 1:3.2 |
| p-diethylbenzene | 1.7 | 1.8 | 1.6 | 2.2 | 1:2 |
| n-dodecylbenzene | 1.7 | 2.7 | 1.8 | Not deter. | 1:2 |
| n-butylbenzene | 2.4 | 3.9 | 2.5 | 2.6 | 1:2 |
| n-pentylbenzene | 2.5 | 3.6 | 2.6 | 3.4 | 1:2 |
| Isobutylbenzene | 2.6 | 3.8 | 2.8 | 3.6 | 1:2 |
| Toluene | 2.8 | 3.5 | 3.2 | 1.5 | 1:2 |
| n-propylbenzene | 2.9 | 4.4 | 3.2 | 2.9 | 1:2 |
| n-heptylbenzene | 2.9 | 3.4 | 2.7 | Not deter. | 1:2 |
| o-methyl n-propylbenzene | 3.4 | 4.9 | 2.2 | 6.4 | 1:2 |
| m-diethylbenzene | 3.4 | 6.0 | 2.3 | 9.3 | 1:2 |
| p-methyl n-propylbenzene | 3.6 | 3.9 | 2.3 | 9.0 | 1:2 |
| n-nonylbenzene | 4.0 | 5.6 | 4.3 | Not deter. | 1:2 |
| o-diethylbenzene | 2.5 | 4.1 | 1.9 | 8.4 | 1:2 |

TABLE 2

Selectivity ($\alpha$) for $C_8$ Aromatics Separation on $Cs_{50}Na_{36}X$
Feed EB:PX:MX:OX:Desorbent
Wt % 22.5:5:5:50:22.5
($C_8$:Desorbent) 1:2 by mole

| Desorbent | eb/px | eb/mx | eb/ox | eb/Des |
|---|---|---|---|---|
| None | 2.5 | 4.1 | 0.9 | |
| Benzene | 0.8 | 1.4 | 1.6 | 0.4 |
| Toluene | 2.1 | 3.0 | 2.5 | 1.7 |
| 1,3,5 Trimethylbenzene | 1.0 | 1.5 | 1.9 | 3.5 |
| 1,2,3 Trimethylbenzene | 2.8 | 3.9 | 1.9 | 4 |
| Prehnitene | 1.8 | 2.2 | 2.1 | 5 |

Tables 1 and 2 demonstrate that some desorbents decrease the selectivities $\gamma$eb/px, $\gamma$eb/mx, $\gamma$eb/ox below two. Other desorbents increase one or more selectivities leaving those remaining almost unchanged.

EXAMPLE 2

This Example is included to demonstrate that ethylbenzene selective zeolites should not be considered in isolation but must be tied to a combination with a desorbent. Toluene has given good overall results in the Examples above. NaX and KX zeolites are ethylbenzene selective. However, together the overall selectivities of NaX or KX and toluene are not acceptable. Those results are shown in Table 3.

TABLE 3

Selectivity ($\alpha$) for $C_8$ Aromatics Separation with NaX and KX
Feed (Equimolar $C_8$ Aromatics): Desorbent

| Zeolite | eb/px | eb/mx | eb/ox | eb/Desorbent | Desorbent | Wt % Desorbent |
|---|---|---|---|---|---|---|
| NaX | 1.2 | 1.2 | 2.6 | — | None | — |
| | 0.8 | 0.8 | 0.8 | 1.6 | Benzene | 70 |
| | 0.9 | 0.9 | 0.8 | 0.8 | Toluene | 65 |
| | 0.8 | 0.8 | 0.5 | 3.4 | 1,4 diethylbenzene | 72 |
| KX | 1.1 | 0.6 | 1.3 | — | None | — |
| | 0.6 | 1.1 | 1.7 | 2.8 | Benzene | 70 |
| | 0.7 | 2.0 | 1.8 | 1.5 | Toluene | 65 |
| | 2.0 | 1.6 | 1.6 | 9.3 | 1,4 diethylbenzene | 72 |

EXAMPLE 3

This Example is included to show that the gallium form of Cs-X is also ethylbenzene selective. A gallium zeolite was produced having a Si/(Al+Ga) ratio of about 1.5. The zeolite contained only traces of aluminum. The comparative Ca(Al)X had a Si/Al ratio of 1.5. These zeolites were tested in the process shown in the above Examples using an equimolar feed. The results of this testing are shown in Table 4.

TABLE 4

| | eb/px | eb/me | eb/ox |
|---|---|---|---|
| Cs(Ga)X | 3.1 | 4.2 | 2.2 |
| Cs(Al)X | 3.3 | 4.1 | 1.8 |

This Example shows that the zeolite is relatively insensitive to the presence or absence of gallium in the tetrahedral framework when used in the claimed service.

In summary, improved separation of ethylbenzene from mixtures of isomeric xylenes are possible by the use of CsX zeolites in combination with certain desorbents.

What is claimed is:

1. A process for the separation of ethylbenzene from a feedstream containing ethylbenzene and at least one xylene isomer comprising the steps of:
   (a) contacting the feedstream with a Cs exchanged Type X zeolite under conditions for adsorbing ethylbenzene by the zeolite,
   (b) passing a desorbent selected from the group consisting of n-propylbenzene, n-butylbenzene, n-pentylbenzene, n-heptylbenzene, n-nonylbenzene, isobutylbenzene, m-diethylbenzene, o-methyl-n-propylbenzene, and p-methyl-n-propylbenzene through the zeolite during and after the contacting step,
   (c) recovering a stream enhanced in ethylbenzene content from the zeolite.

2. The process of claim 1 wherein the feedstream contains orthoxylene, metaxylene, and paraxylene.

3. The process of claim 1 wherein the feedstream is substantially depleted in paraxylene.

4. The process of claim 1 wherein the zeolite contains Na cations.

5. The process of claim 4 wherein the zeolite contains about 50 Cs and 36 Na cations per zeolite repeating unit.

6. The process of claim 2 wherein the desorbent is n-propylbenzene.

7. The process of claim 2 wherein the desorbent is n-butylbenzene.

8. The process of claim 2 wherein the desorbent is n-pentylbenzene.

9. The process of claim 2 wherein the desorbent is n-heptylbenzne.

10. The process of claim 2 wherein the desorbent is n-nonylbenzene.

11. The process of claim 2 wherein the desorbent is isobutylbenzene.

12. The process of claim 2 wherein the desorbent is m-diethylbenzene.

13. The process of claim 2 wherein the desorbent is o-methyl-n-propylbenzene.

14. The process of claim 2 wherein the desorbent is p-methyl-n-propylbenzene.

15. A process for the separation of ethylbenzene from a feedstream containing ethylbenzene and at least one xylene isomer comprising the steps of:
   (a) contacting the feedstream with a Cs exchanged Type X zeolite containing Na cations under conditions for adsorbing ethylbenzene by the zeolite,
   (b) passing n-nonylbenzene through the zeolite during or after the contacting step, and
   (c) recovering a stream enhanced in ethylbenzene concentration from the zeolite.

16. The process of claim 15 wherein the feedstream contains orthoxylene, metaxylene and paraxylene.

17. The process of claim 15 wherein the feedstream is substantially depleted in paraxylene.

* * * * *